(12) United States Patent
Wengreen et al.

(10) Patent No.: US 7,877,151 B2
(45) Date of Patent: Jan. 25, 2011

(54) STRATEGIC COMBINATION OF CONDUCTORS IN A LEAD ASSEMBLY FOR A MEDICAL DEVICE

(75) Inventors: Eric John Wengreen, Blaine, MN (US); Gregory L. Sundberg, Stillwater, MN (US); Russell E. Anderson, Hopkins, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 1019 days.

(21) Appl. No.: 11/063,263

(22) Filed: Feb. 22, 2005

(65) Prior Publication Data

US 2006/0190067 A1   Aug. 24, 2006

(51) Int. Cl.
*A61N 1/00* (2006.01)
(52) U.S. Cl. ..................................... 607/122
(58) Field of Classification Search ............ 607/122, 607/115–116, 119, 123–126, 128–130
See application file for complete search history.

(56) References Cited

U.S. PATENT DOCUMENTS

| | | | |
|---|---|---|---|
| 5,935,159 A | 8/1999 | Cross, Jr. et al. | |
| 6,104,961 A * | 8/2000 | Conger et al. | 607/122 |
| 6,210,407 B1 * | 4/2001 | Webster | 606/41 |
| 6,249,708 B1 | 6/2001 | Nelson et al. | |
| 6,249,709 B1 | 6/2001 | Conger et al. | |
| 6,381,835 B1 | 5/2002 | Conger et al. | |
| 6,402,719 B1 * | 6/2002 | Ponzi et al. | 604/95.04 |
| 6,434,430 B2 * | 8/2002 | Borgersen et al. | 607/122 |
| 6,501,991 B1 * | 12/2002 | Honeck et al. | 607/122 |
| 6,701,191 B2 | 3/2004 | Schell | |
| 6,785,576 B2 | 8/2004 | Verness | |
| 6,925,334 B1 | 8/2005 | Salys | |
| 2002/0099430 A1 * | 7/2002 | Verness | 607/122 |
| 2003/0163184 A1 * | 8/2003 | Scheiner et al. | 607/122 |
| 2004/0260373 A1 * | 12/2004 | Ries et al. | 607/116 |
| 2005/0131507 A1 | 6/2005 | Sundberg | |

* cited by examiner

*Primary Examiner*—Mark W Bockelman
*Assistant Examiner*—Roland Dinga
(74) *Attorney, Agent, or Firm*—Faegre & Benson LLP

(57) ABSTRACT

Low voltage conductors in a lead assembly share a lumen in a tube and are separated from adjacent conductors in the tube by an insulative layer. In an embodiment, low voltage conductors are combined with high voltage conductors. In another embodiment, low voltage conductors are combined with other low voltage conductors.

27 Claims, 10 Drawing Sheets

STRATEGIC COMBINATION OF CONDUCTORS IN A LEAD ASSEMBLY FOR A MEDICAL DEVICE

TECHNICAL FIELD

This application relates generally to lead assemblies for medical devices, and, more particularly, to lead assemblies including conductors that are strategically combined in a lumen.

BACKGROUND

A medical device can be configured to sense an intrinsic electrical signal in the heart and to deliver therapy to the heart. Cardiac stimulation therapies include both low energy therapies and high-energy therapies. Low energy therapies include, for example, cardioversion, anti-tachycardia pacing (ATP) and other types of cardiac resynchronization therapy (CRT). Low energy therapies typically involve sending a low-voltage signal through one or more conductors. High energy therapies such as defibrillation typically involve sending a high-voltage signal through one or more conductors to the heart.

Cardiac sensing and cardiac stimulation usually involve transmitting an electric signal through a conductor that is part of a lead assembly. A lead assembly typically includes an insulative tube and conductors extending through the tube. Improved lead assemblies are needed.

SUMMARY

A medical device lead assembly includes a first high voltage electrode, a second high voltage electrode, and a first low voltage electrode. The first low voltage electrode is located proximate the first high voltage electrode. In an example, the first low voltage electrode is located within 1 inch of the first high voltage electrode. The lead assembly includes a tube having a first lumen and a second lumen. A first high voltage conductor extends through the first lumen and is coupled to the first high voltage electrode. A second high voltage conductor extends through the second lumen and is coupled to the second high voltage electrode. A first low voltage conductor extends through the first lumen and is electrically insulated from the first high voltage conductor. The first low voltage conductor is coupled to the first low voltage electrode. In an example, the medical device lead assembly also includes a second low voltage electrode proximate the first high voltage electrode, and a second low voltage conductor extending through the first lumen and coupled to the second low voltage electrode. In an example, the first low voltage conductor includes a conductive coil and an insulative sheath extending over the conductive coil. In an example, the conductive coil is rotatable in the sheath with respect to an axis that is substantially parallel to an axis of the tube and the lumen resists rotational movement of insulative sheath relative to the tube when the coil is rotated. In an example, the lead assembly is coupled to a defibrillator.

In another example, a medical device lead assembly includes a tube having a first lumen, a second lumen, and a third lumen, a first high voltage conductor extending through the first lumen, a second high voltage conductor extending through the second lumen, a first low-voltage conductor extending through the third lumen, and a second low-voltage conductor extending through the third lumen, the second low-voltage conductor electrically insulated from the first low-voltage conductor. In an example, the first low-voltage conductor includes a coil and an insulative sheath over the coil, and the third lumen includes internal surfaces configured to hold the first low-voltage conductor and the second low-voltage conductor in a substantially fixed position with respect to the tube.

An example method includes extending a first high voltage conductor coupled to a first high voltage electrode through a first lumen in an insulative tube for a medical device lead assembly, extending a second high voltage conductor coupled to a second high voltage electrode through a second lumen in the insulative tube, extending through the first lumen in the insulative tube a first low voltage conductor coupled to a first low voltage electrode proximate the high first high voltage electrode, and electrically insulating the first low voltage conductor from the first high voltage conductor, wherein the first low voltage conductor is electrically isolated from the first high voltage conductor. In an example, the method further includes extending through the first lumen in the insulative tube a second low voltage conductor coupled to a second low voltage electrode; and electrically insulating the second low voltage conductor from the first high voltage conductor and the first low voltage conductor. In another example, the method further includes extending a second low voltage conductor coupled to a second low voltage electrode through the second lumen in the insulative tube, and electrically insulating the second low voltage conductor from the second high voltage conductor.

Another method includes extending a first high voltage conductor coupled to a first high voltage electrode through a first lumen in an insulative tube for a medical device lead assembly, extending a second high voltage conductor coupled to a second high voltage electrode through a second lumen in the insulative tube, extending a first low voltage conductor coupled to a first low voltage electrode through a third lumen in the insulative tube, extending a second low voltage conductor coupled to a second low voltage electrode through the third lumen in the insulative tube, and electrically insulating the first low voltage conductor from the second low voltage conductor. In an example, the first high voltage electrode and second high voltage electrode are defibrillation electrodes.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

DETAILED DESCRIPTION

Figure 1:
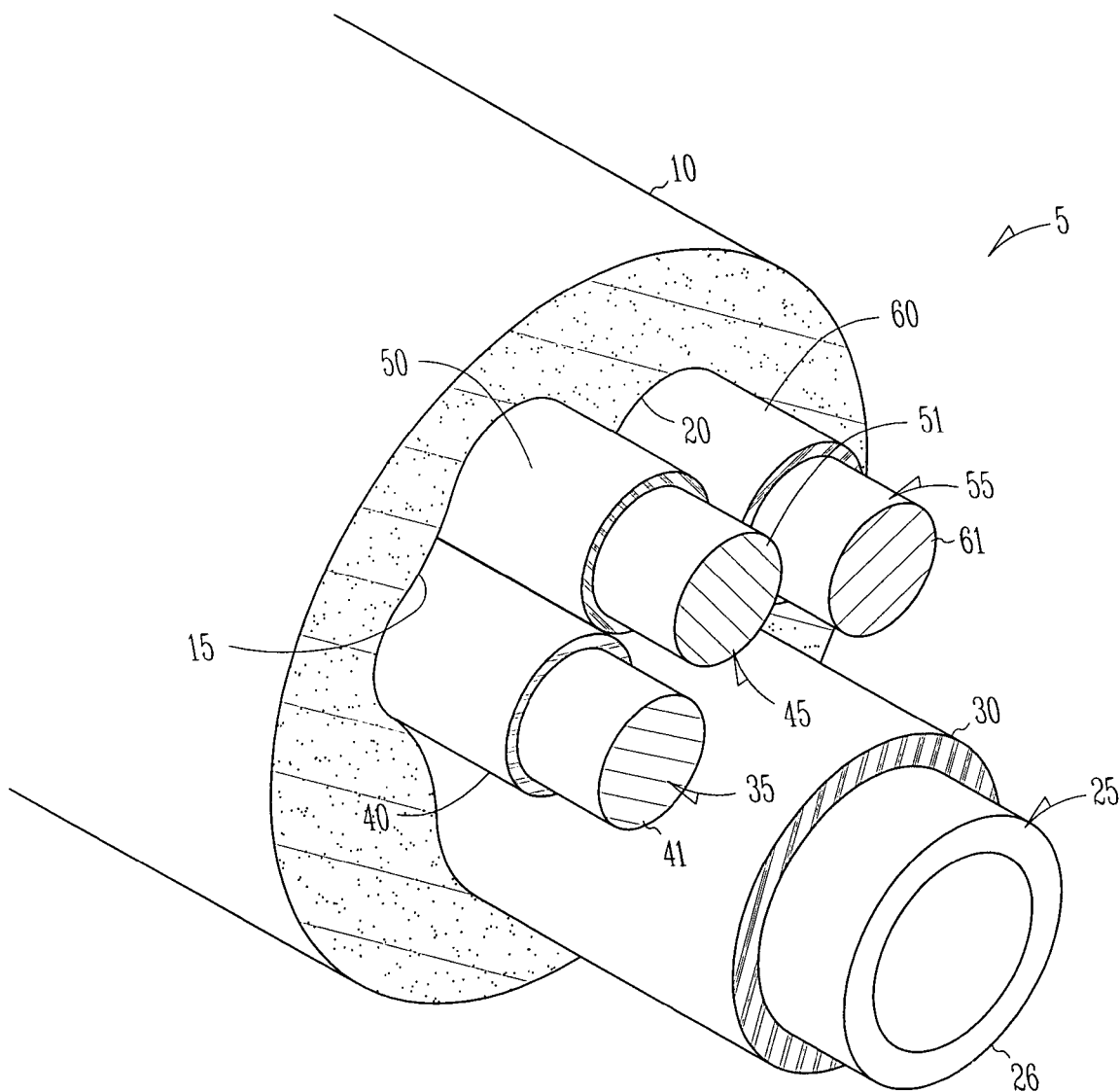
FIG. 1 is a perspective view of a lead assembly including a tube and conductors.

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference.

An example lead assembly includes a tube having lumens and conductors that extend through the lumens. Conductors are combined in the lumens, as shown, for example, in FIG. 1. In an example, conductors are combined in lumens based upon the relative proximity of electrodes that are coupled to the conductors and the voltages delivered or sensed by the electrodes. In an example, the strategic combination of high and low voltage conductors in lumens allows for reduction in the diameter of the lead assembly. In an example, high voltage conductors extend through separate lumens in the tube, i.e. the high conductors do not share the same lumen. The tube material that separates the lumens insulates the high voltage conductors from each other. Low voltage conductors can be combined with other conductors in a lumen. In an example, one or more low voltage conductors is combined with a high voltage conductor, as shown in FIGS. 1, 5A, 5B, and 5C. In another example, low voltage conductors are combined together in a lumen, without a high voltage conductor, as shown in FIGS. 6A and 6B. As used herein, "high voltage" conductors refers to conductors that are configured to conduct current at high voltages, as is required during defibrillation therapy, for example. "Low voltage" conductors refers to conductors that are configured for low-voltage functions, such as sensing and pacing. In an example, high voltage and low voltage conductors are the same size and have the same material composition. In another example, the size or material composition of the conductors varies.

At least one layer of insulation is provided between each low voltage conductor and each other conductor that shares a lumen with the low voltage conductor. In varying examples, a layer of insulation is provided on each of the conductors, or on only some of the conductors. In one example, a low voltage conductor includes an insulative layer. In another example, a particular low voltage conductor does not have an insulative layer, but an adjacent high or low voltage conductor includes an insulative layer. High voltage conductors are extended through separate lumens, so that the tube material between the lumens provides insulation between the high voltage conductors.

In an example, at low voltages such as the voltages used for pacing or sensing, the insulative layer on at least one of a pair of adjacent conductors prevents shorts between the conductors. At high voltages, conductors that are connected to electrodes that are in close proximity are generally at similar potentials because of conduction through the body between the electrodes. In an example, while a defibrillation therapy is delivered, a pacing electrode that is in close proximity to a defibrillation coil will be at a voltage that is approximately the same as the defibrillation coil. Because there is only a small voltage difference between the conductor that is connected to the pacing electrode and the conductor that is connected to the defibrillation coil, the layer of insulation on one or both of the conductors is sufficient to prevent shorts, and these two conductors can be extended through the same lumen.

Figure 3A:
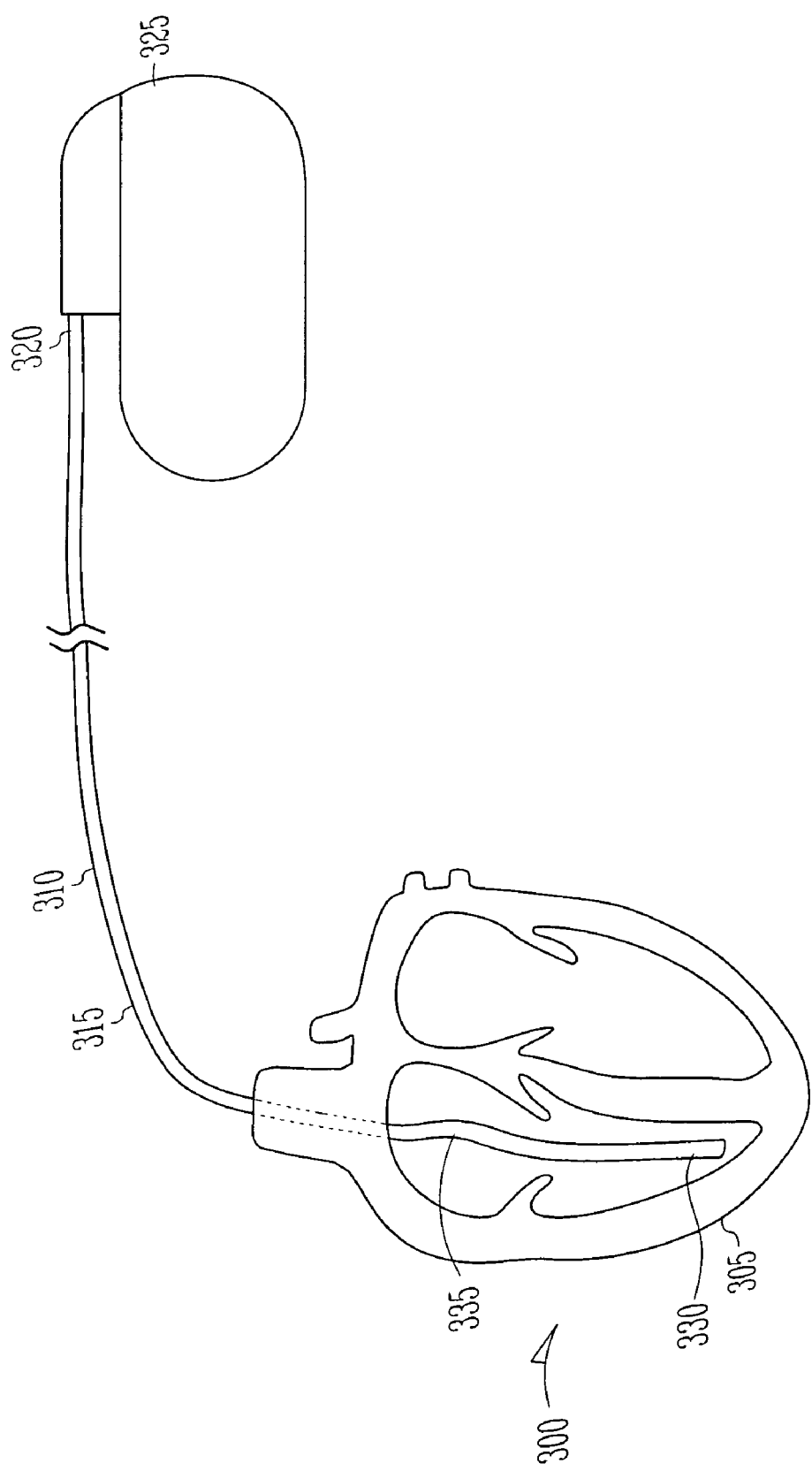
FIG. 3A-3B shows example systems for monitoring and stimulating the heart.
Figure 3B:
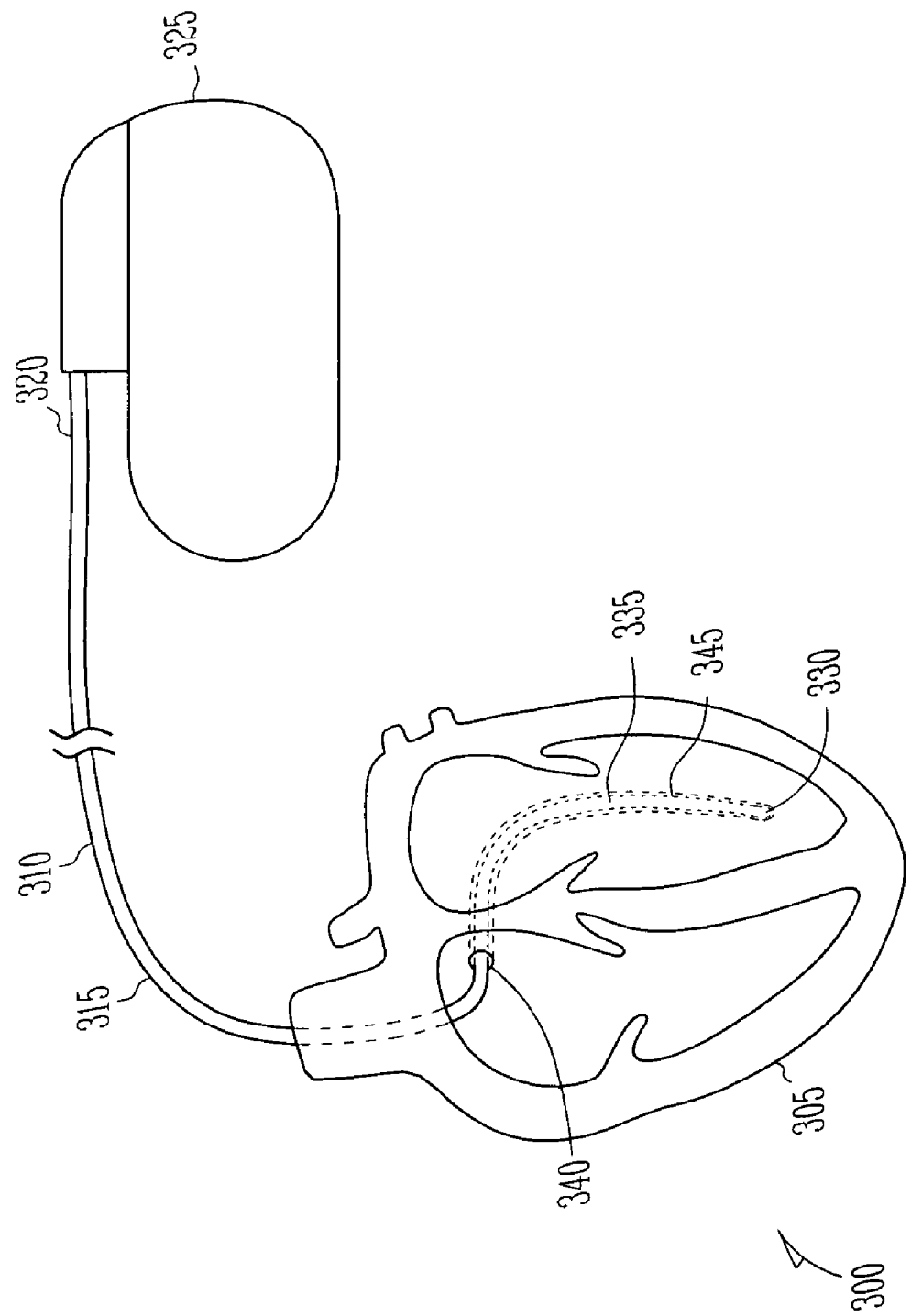

FIGS. 3A and 3B show an example system 300 that includes a lead assembly 310 for monitoring and stimulating a heart 305. The lead assembly 310 includes a lead body 315 and a plurality of conductors (not shown) that connect at a proximal end 320 to a medical device 325. In an example, the medical device 325 includes a pulse generator. A distal end 330 of the lead assembly is implanted in or around the heart 305. In an example, the distal end 330 and intermediate portion 335 are inserted into the right side of the heart, as shown in FIG. 3A. In an example, the intermediate portion extends through the right atria and the distal end is in the right ventricle. In another example, the distal end 330 and an intermediate portion 335 are inserted into the coronary sinus 340 and cardiac vein 345, as shown in FIG. 3B.

Referring again to FIG. 1, an example lead assembly 5 includes a tube 10 that has first and second lumens 15, 20 that extend longitudinally through the tube. In an example, the tube is formed from a polymer, such as silicone. A first low voltage conductor 25 extends through the first lumen 15. In an example, the first low voltage conductor 25 includes a conductive coil 26 and insulative sheath 30. In an example, the low voltage conductor 25 connects to an electrode that is used for sensing, pacing, or both sensing and pacing. In an example, the coil 26 is rotatable within the lumen 15.

A first high voltage conductor 35 also extends through the first lumen 15. The first high voltage conductor 35 includes an insulative outer layer 40 and a conductive core 41. In an example, the first high voltage conductor 35 is part of a system configured to stimulate the heart, such as an antitachyarrhythmia therapy system. In an example antitachyarrhythmia therapy system, the high voltage conductor 35 carries current to a defibrillation coil or other type of antitachyarrhythmia electrode. An electrode coupled to the first high voltage conductor 35 is proximate to an electrode coupled to the first low voltage conductor 25.

A second low voltage conductor 45 also extends through the fist lumen 15. In an example, the second low voltage conductor 45 includes an insulative outer layer 50 and a conductive core 51. The second low voltage conductor 45 is coupled to an electrode that is proximate the electrode coupled to the first high voltage conductor.

A second high voltage conductor 55 extends through the second lumen 20. In an example, the second high voltage conductor includes an insulative outer layer 60 and a conductive core 61. In varying examples, the second high voltage conductor is connected to a second defibrillation electrode or other antitachyarrhythmia therapy apparatus.

In an example, the insulative outer layers 40, 50, 60 include ethylene-tetrafluoroethylene (ETFE) or polytetrafluoroethylene (PTFE), preferably ETFE. At low voltages, the insulative properties of the outer layers are adequate to prevent electrical shorts, and the high voltage electrodes are electrically isolated from adjacent low voltage electrodes. For example, the voltages encountered during sensing and pacing are typically low enough that the insulative layer is adequate. When a therapeutic high voltage signal is delivered, the voltage in one or more of the low voltage conductors is at or near the therapeutic voltage. In an example, a low-voltage conductor that is coupled to an electrode that is in close proximity to a high-voltage electrode is at or near the voltage of the high-voltage electrode due to conduction through the body. Thus, the insulation between low and high voltage conductors that are in sufficiently close proximity does not need to be rated for the high potentials of therapeutic signals. In an example, the insulation is selected to provide an insulation breakdown voltage that exceeds the voltage difference between adjacent low and high voltage conductors during defibrillation. "Insulation breakdown voltage" refers to the voltage at which conduction occurs between the conductors, through the insulation. In one example, insulation is selected to effectively isolate low voltage conductors and high voltage conductors that are coupled to electrodes that are positioned within 1 inch of each other on a lead. In another example, insulation is selected to effectively isolate low voltage conductors and high voltage conductors that are coupled to electrodes that are positioned within ½ inch of each other on a lead.

Referring again to FIG. 1, in an example, during delivery of a high voltage therapy, there is a voltage difference between the high voltage conductor 35 and the low voltage conductor 45. In an example, the voltage difference between electrodes during defibrillation is a function of the distance between the electrodes. The voltage difference between the electrodes is typically also affected by other factors, such as the therapeutic voltage and impedance of tissue or body fluids between the electrodes. In an example, the insulative outer layer 40 on the high voltage conductive core 41 effectively isolates the low voltage conductor from the high voltage conductor below the breakdown voltage of the insulative outer layer. In an example, the high and low voltage conductors 35, 45 are extended through a common lumen if the maximum voltage difference between the conductors during defibrillation does not exceed the breakdown voltage of the insulative layer 40 between the conductors.

In another example, the distance between high and low voltage electrodes coupled to the respective high and low voltage conductors 35, 40 is controlled to avoid generating a voltage difference that exceeds the breakdown voltage of the insulative layer 40 between the high and low electrodes. In an example, a predetermined distance between the low and high voltage electrodes is selected so that the maximum voltage difference generated during defibrillation does not exceed the insulation breakdown voltage.

Figure 2:
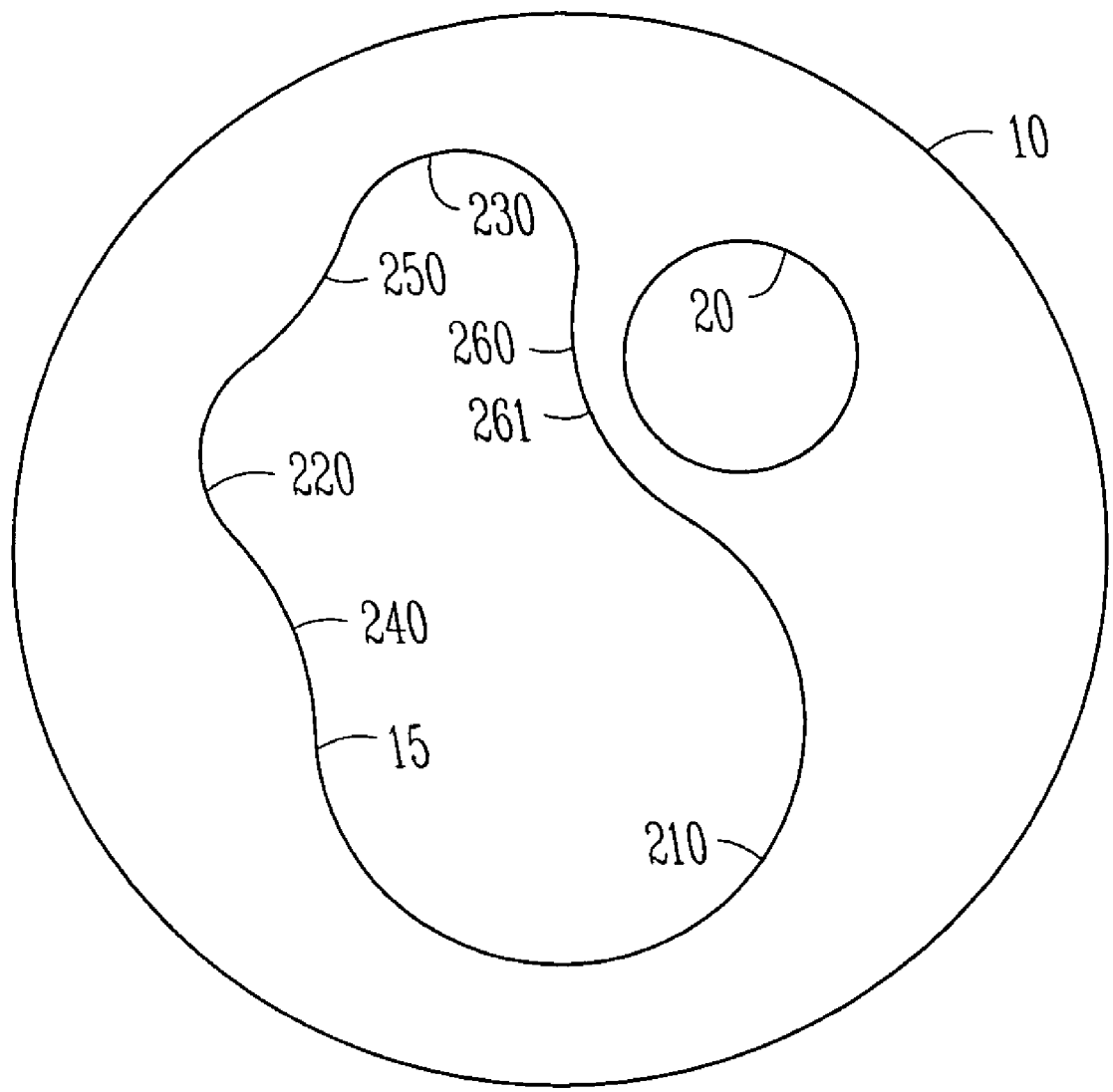
FIG. 2 is an end view of the tube shown in FIG. 1.

Referring now to FIG. 2, an end view of the tube 10 shown in FIG. 1 shows the profile of the first lumen 15 and second lumen 20. In an example, the first lumen has surfaces that are configured to contact exterior surfaces of the conductors that extend through the first lumen. In an example, a first inner surface 210 of the first lumen 15 fits with a portion of the outer shape of the insulative sheath 30 (shown in FIG. 1) that extends over the first low voltage conductor 25 of FIG. 1. In an example, the first inner surface 210 is shaped to resist radial or rotational movement of the sheath. The surface 210 does not necessarily eliminate all movement of the conductor 25. In an example, a plurality of points or lines on the first inner surface 210 contact a plurality of respective points or lines on a portion of the outer shape of the insulative sheath. In another example, the first inner surface 210 roughly tracks a portion of the outer shape of the insulative sheath. In another example, the first inner surface 210 closely matches a portion of the outer shape of the insulative sheath 30. In an example, the profile of the first inner surface 210 defines a partial circle.

In an example, a second inner surface 220 of the first lumen 15 is configured to contact the outer surface of the first high voltage conductor 35, and a third inner surface 230 of the first lumen 15 is configured to contact the outer surface of the low voltage conductor 45. In an example, the first lumen includes additional inner surfaces that are configured to contact outer surfaces of one or more of the conductors 25, 35, 45 or additional conductors.

In an example, the inner surfaces 210, 220, 230 resist rotational or radial movement of the conductors 25, 35, 45 relative to the tube 10. For example, the inner surfaces 210, 220, 230 can be configured to hold the coil 26 such that the rotation axis of the coil is substantially fixed with respect to the tube 10. In an example, the inner surfaces 210, 220, 230 do not eliminate all movement of the conductors 25, 35, 45, but do restrict the movement enough that the conductors do not get tangled or bound with each other. In an example, the inner surfaces 210, 220, 230 define three partial cylinders that have respective diameters that are approximately the same as respective diameters of the conductors that extend through the cylinders. In another example, the inner surfaces 210, 220, 230 define contours of the lumen that do not precisely match the outer shapes of the conductors 25, 35, 45, but merely sufficiently conform to the respective outer surfaces of the conductors to resist or prevent twisting or binding of the conductors if the coil 26 is turned. In an example, the first lumen 15 is slightly larger than the collective cross-section of the conductors 25, 35, 45 to allow the conductors to be pulled through the lumen. In another example, the first lumen 15 is slightly smaller than the conductors 25, 35, 45, and the tube 10 is made from an elastic material that stretches to accommodate the conductors in the lumen. In another example, the tube 10 is co-extruded with the conductors 25, 35, 45.

Referring again to FIG. 2, in an example, connecting surfaces 240, 250, 260 connect the various inner surfaces. In an example, connecting surfaces 240, 250, 260 are blended with the inner surfaces 210, 220, 230. In an example, the connecting surfaces 240, 250, 260 are shaped to further restrict the movement of the conductors 25, 35, 40. In an example, when the tube is bent to a defined radius, the connecting surfaces 240, 250, 260 contact the conductors 25, 35, 45 and restrict the movement of at least one of the conductors. In an example, second lumen 20 is positioned proximate a bulge 261 in the first lumen. In an example, the presence and location of the second high voltage conductor 55 provides resistance against radial or angular movement of the conductors in the first lumen. In an example, the presence and location of the second high voltage conductor 55 in the second lumen prevents excessive twisting of the tube when one of the conductors in the first lumen is rotated. In an example, resistance against twisting of the tube is provided when a coil 26 is rotated inside a sleeve.

In varying examples, the conductors 25, 35, 45 are connected to one or more of variety of components, including electrodes that can be used for pacing, sensing, defibrillation, or other purposes. For example, the lead assembly shown in FIG. 1 and the tube shown in FIG. 2 can be used in a system that is configured to monitor an intrinsic electrical heart signal and deliver an arrhythmia therapy, such as the system shown in FIG. 3.

Figure 4A:
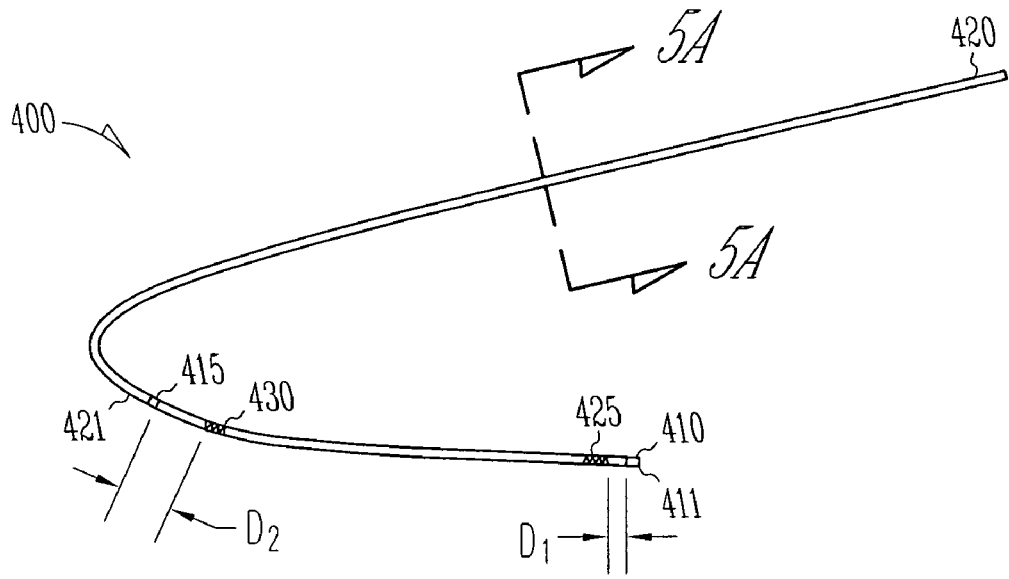
FIG. 4A-4C show example lead assemblies.
Figure 4B:
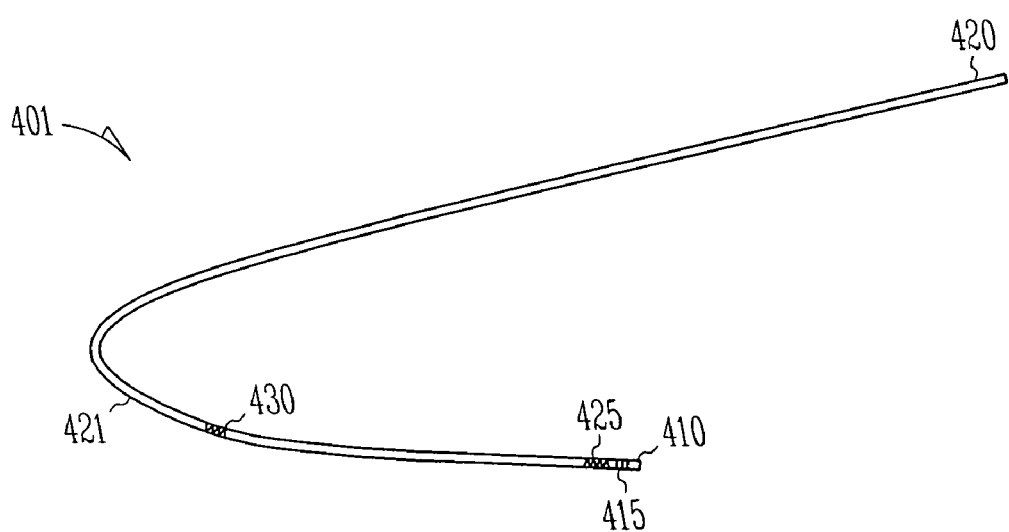
Figure 4C:
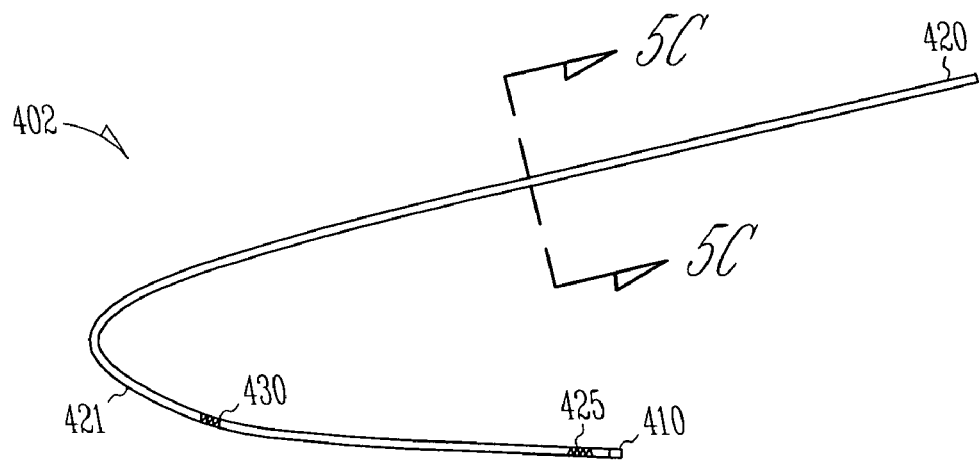

FIG. 4A-4C provide a schematic illustrations of example lead assemblies 400, 401, 402. FIG. 4A shows a lead assembly 400 that includes a distal electrode 410. In an example, the distal electrode 410 is at the distal end 411 of the lead assembly 400. A second electrode 415 at an intermediate portion 421 of the lead assembly. Both electrodes 410, 415 can be used for pacing or sensing. In an example, the distal electrode 410 is a pacing cathode and the second electrode 415 is a pacing anode. In another example, the distal electrode 410 is a pacing anode and the second electrode 415 is a pacing cathode. The lead assembly also includes antitachyarrhythmia therapy coils 425, 430. In an example, coil 425 is a defibrillation anode and coil 430 is a defibrillation cathode. In another example, coil 425 is a defibrillation cathode and coil 425 is a defibrillation anode. In an example, during an anti-tachyarrhythmia therapy, coil 425 is at +400 volts and coil 430 is at −400 volts. The lead assembly also includes conductors that connect to the electrodes 410, 415 and the antitachyarrhythmia coils 425, 430. A proximal end 420 of the lead assembly is configured to connect to a medical device that includes, for example, sensing circuitry and pulse generating circuitry, such as the device shown in FIG. 1. In an example, the conductors that are connected to the electrode 410 and coil 425 are combined in a lumen in the lead. In an example, the electrodes 410 and 425 are at approximately the same voltage during a defibrillation pulse. In an example, the electrodes 410 and 425 are close enough together that the difference in voltage between the electrodes is less than the breakdown voltage of the insulation between the conductors that are coupled to the electrodes. In an example, the distance $D_1$ between electrode 410 and electrode 425 is approximately 1 inch. In another example, the distance $D_1$ between electrode 410 and electrode 425 is approximately ½ inch. The distance $D_1$ between electrodes 410 and 425 can be increased if the breakdown voltage of the insulation between the conductors is increased.

In another example, the conductors that are connected to the electrode 415 and coil 430 are combined in a second lumen. In an example, the electrodes 415 and 430 are close enough together that the difference in voltage between the electrodes is less than the breakdown voltage of the insulation between the conductors that are coupled to the electrodes. In an example, the distance $D_2$ between electrode 415 and electrode 430 is approximately 1 inch. In another example, the distance $D_2$ between electrode 415 and electrode 430 is approximately ½ inch.

FIG. 4B shows a lead assembly 401 having a second electrode 415 that is located near the distal end of the lead. In an example, the lead assembly shown in cross section in FIG. 1 is configured as shown in FIG. 4B. In an example, conductor 25 is coupled to electrode 410, conductor 35 is coupled to coil 425, conductor 45 is coupled to electrode 415, and conductor 55 is coupled to coil 430. It should be noted that in this example electrodes 410, 415 are in close proximity to coil 425. In an example, the conductors that are coupled to the electrodes 410, 415 extend in a lumen with the conductor that is coupled to the coil 425. In an example, electrodes 410 and 415 are located with one inch of electrode 425.

FIG. 4C shows a lead assembly 402 that does not include a second electrode. In an example, during pacing, electrode 410 is a pacing electrode and coil 425 is a pacing cathode. In an example, the conductor that is connected to electrode 410 is combined in a lumen with coil 425, which is in relatively close proximity to the electrode 410 and therefore at approximately the same voltage during high energy therapy such as defibrillation.

Figure 5A:
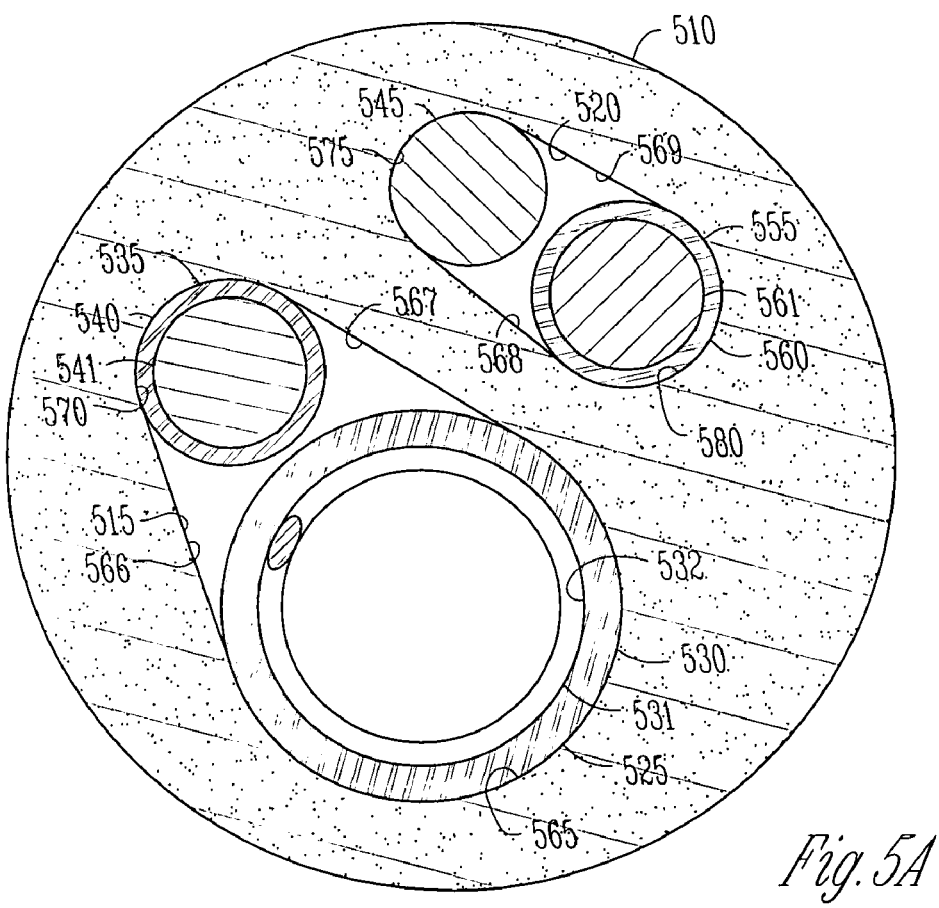
FIG. 5A is a cross section of a lead assembly in which high voltage conductors are combined with low voltage conductors.
Figure 6A:
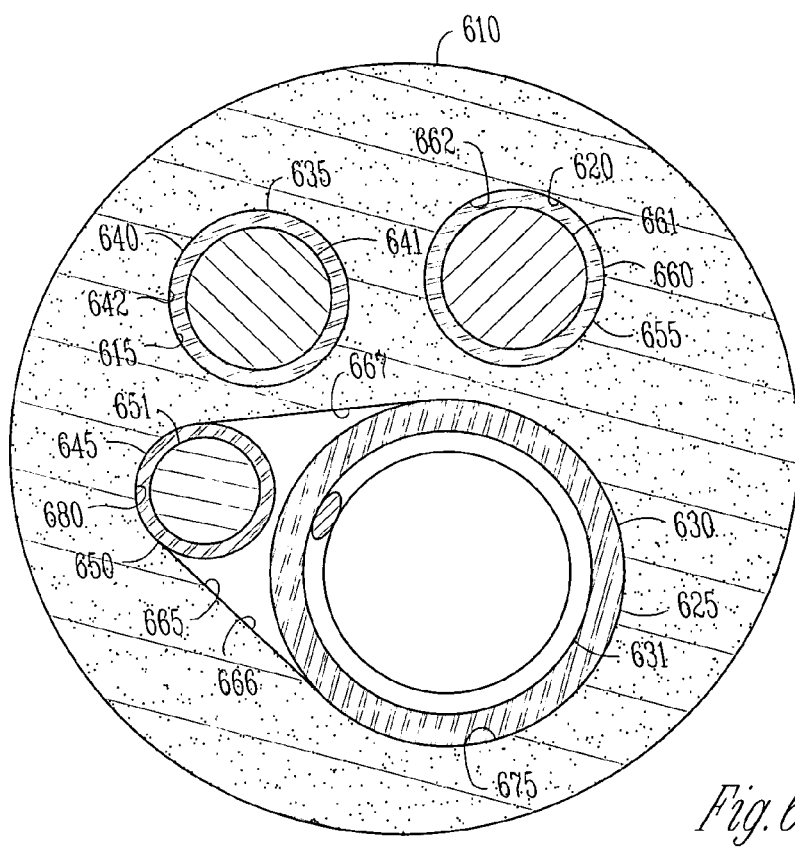
FIG. 6A is a cross section of a lead assembly in which conductors coupled to sensing or pacing electrodes are combined in a lumen.
Figure 6B:
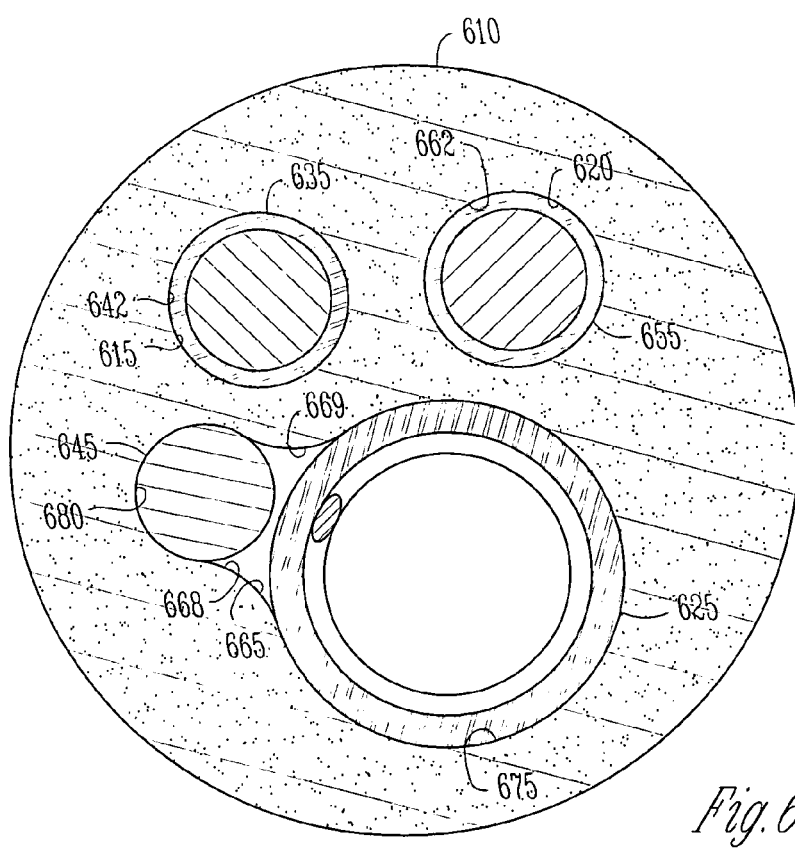
FIG. 6B is a cross section of a lead assembly in which conductors coupled to sensing or pacing electrodes are combined in a lumen.

Referring now to FIG. 5A, a cross section of an example lead assembly is shown. In an example, the cross section is taken at 5A-5A of the lead assembly shown in FIG. 4A. A tube 510 includes a first lumen 515 and a second lumen 520. A first conductor 525 extends through the first lumen 515. A second conductor 535 extends through the first lumen adjacent to the first conductor 525. In an example, the first conductor 525 is a sensing conductor that includes a conductive coil 531 and an insulative outer sheath 530 extending over the conductive coil 531. In another example, the first conductor 525 is connected to a pacing electrode. In another example, a single electrode used for both pacing and sensing is connected to the first conductor 525. In an example, the second conductor 535 is a first high-voltage conductor that includes an insulative outer layer 540 and a conductive core 541.

The first lumen 515 includes a first interior surface 565 that is configured to contact the exterior surface of the first conductor 525 and a second interior surface 570 that is configured to contact the exterior surface of the second conductor 535. In varying other examples, the first lumen includes additional interior surfaces that reflect the exterior surface of the second conductor. In an example, the first and second interior surfaces 565, 570 are configured to restrict the movement of the first conductor and the second conductor with respect to each other. In an example, the first interior surface is configured to restrict the rotational movement of the outer sheath 530 with respect to the tube 5 10, and the outer sheath 530 includes a low-friction inner surface 532 that allows the coil 531 to rotate in the sheath. In an example, the first interior surface 565 defines a first partial cylinder having a first diameter and the second interior surface 570 defines a partial cylinder having a second diameter that is smaller than the diameter of the first partial cylinder. In an example, the first diameter of the partial cylinder defined by the first interior surface is approximately the same as the diameter of the outer surface of the first conductor 525, and the second diameter of the second partial cylinder defined by the second interior surface is approximately the same as the diameter of the outer surface of the second conductor 535. In an example, the insulative layer 540 on the first high voltage conductor touches the outer sheath 530 on the sensing conductor 525. In an example, straight walled sections 566, 567 connect the first interior surface 565 and second interior surface 570. In another example illustrated in FIG. 5B, curved wall sections 576, 577 extend inwardly into the spaced defined by the first lumen 516 and connect the first interior surface 565 and second interior surface 570. In an example, the curved wall sections 576, 577 provide additional structural support compared to the straight-walled example shown in FIG. 5A. The additional structural support further restricts the movement of the first and second conductors 525, 535.

Referring again to FIG. 5A, second lumen 520 extends adjacent to the first lumen 515. Third conductor 545 and fourth conductor 555 extend through the second lumen 520. In an example, the third conductor 545 is connected to a pacing electrode. In another example, the third conductor 545 is connected to a sensing electrode. In another example, a single electrode used for both pacing and sensing is connected to the third conductor 545. In an example, the third conductor 545 does not include an insulative outer layer, as shown in FIG. 5A. In an alternative example, shown in FIG. 5B, the third conductor 545 includes an insulative outer layer 550 and a conductive core 551. The fourth conductor 555 extends through the second lumen 520 adjacent to the third conductor. In an example, the fourth conductor 555 is high voltage conductor and the third conductor is low voltage conductor 545. In an example, the fourth conductor includes an insulative outer layer 560 and a conductive core 561. In an example, the fourth conductor is connected to a defibrillation electrode.

Referring again to FIG. 5A, the second lumen 520 includes a first interior surface 575 that is configured to contact the outer surface of the second low voltage conductor 545. The second lumen 520 also includes a second interior surface 580 that is configured to contact the outer surface of the second high voltage conductor 555. In an example, the first interior surface 575 and the second interior surface 580 restrict the movement of the third conductor 545 and the fourth conductor 555. In an example, the first interior surface 575 of the second lumen 520 defines a first partial cylinder and the second interior surface 580 of the second lumen defines a second partial cylinder that has a diameter that is larger than the diameter of the first partial cylinder of the second lumen. In an example, the diameter of the first partial cylinder is approximately the same as the outer diameter of the third conductor 545 and the diameter of the second partial cylinder is approximately the same as the outer diameter of the fourth conductor 555. In another example, the first interior surface 575 and second interior surface 580 define partial non-cylindrical cross-sections, such as partial ovals, for example. In an example, the third conductor 545 touches the fourth conductor 555. In an example, the second lumen includes flat walls 568, 569 that connect the first interior surface 575 of the second lumen 520 and second interior surface 580 of the second lumen. In an alternative example, shown in FIG. 5B, the second lumen 521 includes curved surfaces 578, 579 that connect the first interior surface 575 and second interior surface 580. In an example, the curved surfaces 578, 579 define a narrowed portion in which the distance between the curved surfaces 578, 579 is less than the diameter of the third conductor 545 and less than the diameter of the fourth conductor 555. In an example, the curved surfaces further restrict the movement of the conductors 545, 555 with respect to each other and with respect to the tube 510.

Figure 5B:
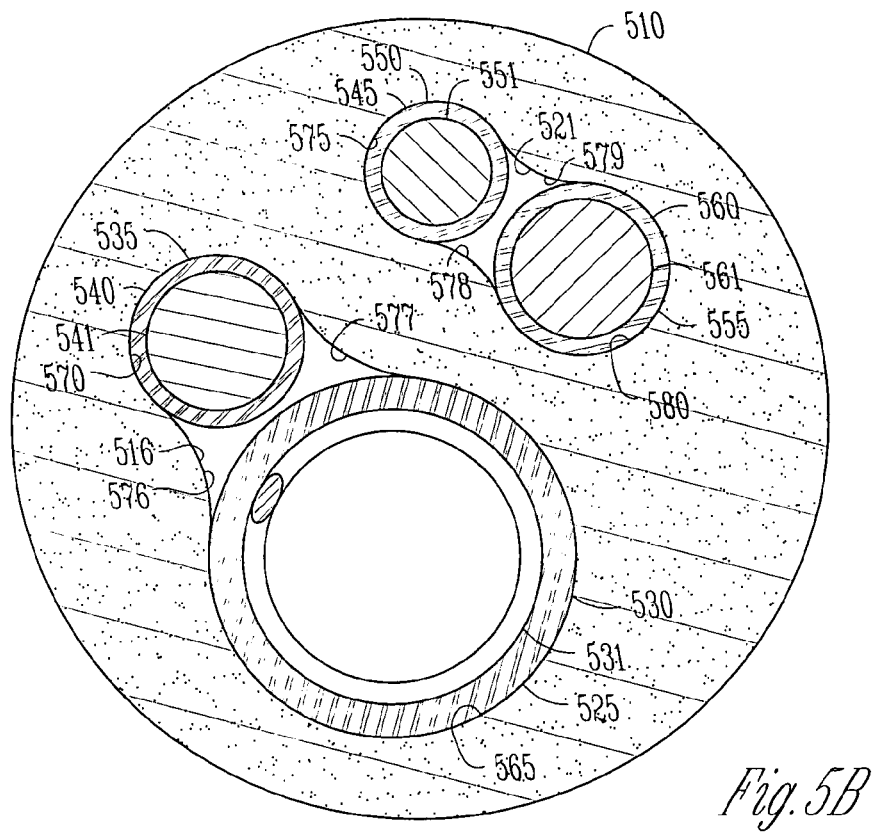
FIG. 5B is a cross section of a lead assembly in which high voltage conductors are combined with low voltage conductors.

In an example, a lead assembly shown in cross section in FIG. 5A or 5B is configured as shown in FIG. 4A, with low voltage conductor 525 coupled to electrode 410, high voltage conductor 535 coupled to coil 425, low voltage conductor 545 coupled to electrode 415, high voltage conductor 555 coupled to coil 430.

Figure 5C:
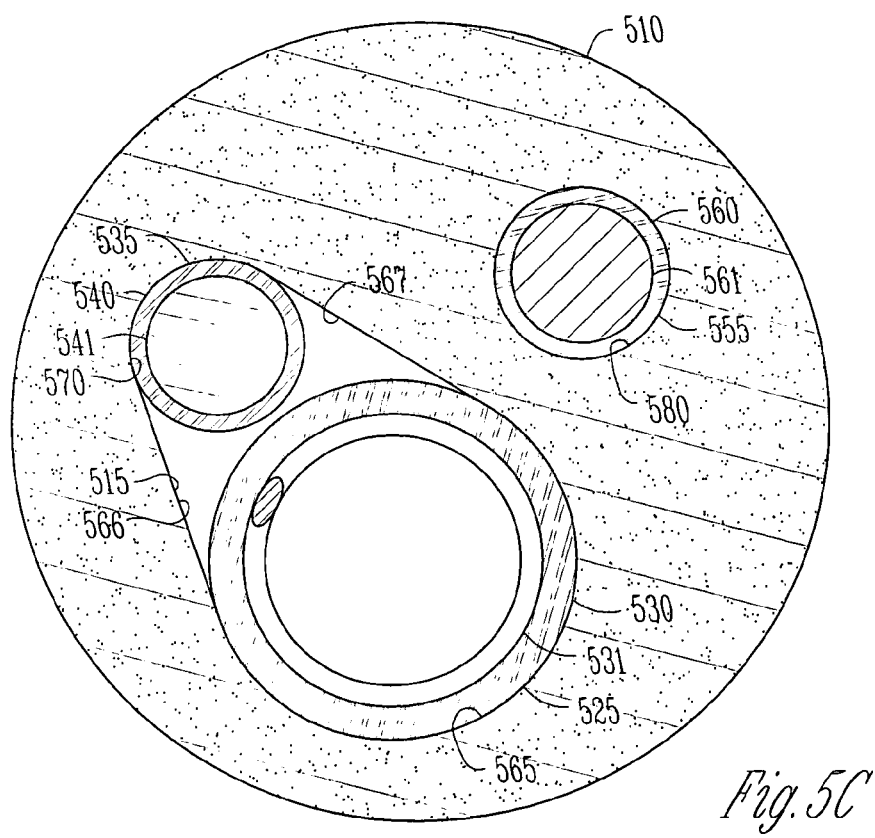
FIG. 5C is a cross section of a lead assembly having one low voltage conductor and two high voltage conductors.

FIG. 5C shows a cross section of a lead assembly having two high voltage conductors 535, 555 and one low voltage conductor 525. In an example, the cross section is taken at 5C-5C of the lead assembly shown in FIG. 4C. Low voltage conductor 525 extends through a lumen 515 with high voltage conductor 535. In an example, the lead assembly shown in cross section in FIG. 5C is configured as shown in FIG. 4C, with electrode 410 coupled to low voltage conductor 525, coil 425 coupled to high voltage conductor 535, and coil 430 coupled to high voltage conductor 555.

Referring now to FIG. 6A, a cross section of another example lead assembly is shown. In an example, the cross section is taken at 5A-5A of the lead assembly shown in FIG. 4A. FIG. 6A shows a cross section of a lead assembly in which high voltage conductors extend through separate lumens and low voltage conductors share a lumen. A tube 610 includes a first lumen 615, a second lumen 620, and a third lumen 665. A first high voltage conductor 635 extends through the first lumen 615. The first high voltage conductor 635 includes an insulative outer layer 640 and a conductive core 641. A second high voltage conductor 655 extends through the second lumen 620. The second high voltage conductor 655 includes an insulative outer layer 660 and a conductive core 661. In an example, the first and second high voltage conductors 635, 655 are connected to antitachyarrhythmia therapy electrodes, such as defibrillation electrodes. In an example, the first lumen 615 includes an interior surface 642 that is configured to contact the outer surface of the first high voltage conductor 635 and the second lumen 620 includes an inner surface 662 that is configured to contact the outer surface of the second high voltage conductor 655. In an example the first and second lumens 615, 620 include interior surfaces that define first and second cylinders having first and second diameters that are approximately the same as the diameters of cylindrical first and second high voltage conductors 635, 655.

Referring again to FIG. 6A, a first low voltage conductor 625 and a second low voltage conductor 645 extend through the third lumen 665. In an example, the first low voltage conductor 625 includes a conductive coil 630 and an insulative sheath 631 extending over the conductive coil. In an example, the second low voltage conductor 645 includes an insulative outer layer 650 and a conductive core 651. In an example, the first low voltage 625 conductor is a sensing conductor, i.e. it is coupled to a sensing electrode. In another example, the first low voltage 625 is connected to a pacing electrode. In another example, a single electrode used for both pacing and sensing is connected to the first low voltage 625. In an example, the second low voltage 645 conductor is a pacing conductor, i.e. it is connected to a pacing electrode. In another example, the second low voltage 645 is connected to a sensing electrode. In another example, a single electrode used for both pacing and sensing is connected to the second low voltage 645. In an example, the first low voltage conductor and second low voltage conductor are both used for both sensing and pacing.

Referring again to FIG. 6A, the third lumen includes first and second interior surfaces 675, 680 that reflect the shape of the outer surfaces of the respective first and second low voltage conductors 625, 645. In an example, the first interior surface 675 defines a partial cylinder that has a diameter that is approximately the same as the diameter of the outer surface of first low voltage conductor 625, and the second interior surface 680 defines a partial cylinder that has a diameter that is approximately the same as the diameter of the outer surface of the second low voltage conductor 645. In an example, the third lumen includes flat walls 666, 667 that connect the first and second interior surfaces 675, 680. In another example, shown in FIG. 6B, the third lumen includes curved surfaces 668, 669 that extend inwardly to define a narrowed portion of the lumen. In an example, the distance between the curved surfaces 668, 669 is less than the diameter of a cylinder defined by the second interior surface 680 of the third lumen. In an example, the curved surfaces 668, 669 restrict the movement of the conductors 625, 645. For example, the interior surfaces 675, 680 can be configured to surround enough of a coil such that the rotation axis of the coil is substantially fixed with respect to the tube. In another example, the second low voltage conductor 645 contacts the first low voltage conductor and further restricts movement of the first low voltage conductor in the lumen.

In an example, a lead assembly shown in cross section in FIG. 6A or 6B is configured as shown in FIG. 4A or 4B, with high voltage conductor 635 coupled to coil 425, high voltage conductor 655 coupled to coil 430, low voltage conductor 625 coupled to electrode 410, and low voltage conductor 645 coupled to electrode 415. Other configurations are possible. For example, high voltage conductor 635 can be coupled to coil 430 and high voltage conductor 644 coupled to coil 425.

In another example, low voltage conductor 625 is coupled to electrode 415, and low voltage conductor 645 coupled to electrode 410.

Figure 7:
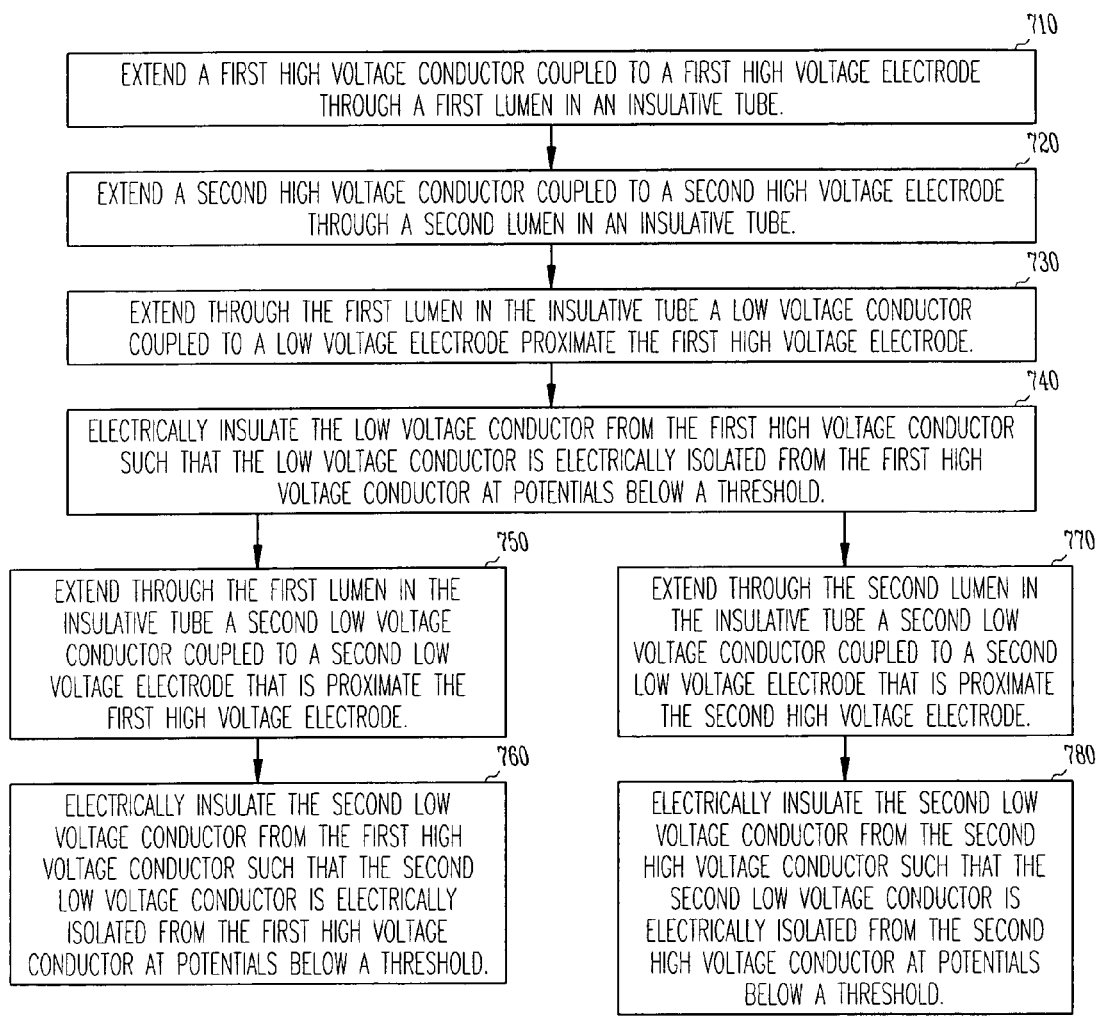
FIG. 7 is flow chart that illustrates a method of combining conductors in lumens in a lead assembly.

FIG. 7 illustrates an example method of combining conductors in lumens in a lead assembly. At 710, a high voltage conductor is coupled to a first electrode through a first lumen in an insulative tube. At 720, a second high voltage conductor is coupled to a second electrode through a second lumen in an insulative tube. The insulative tube provides an insulative layer between the first high voltage conductor and the second high voltage conductor. At 730, a low voltage conductor is coupled through the first lumen in the insulative tube to a low voltage electrode proximate the first high voltage electrode. At 740, the low voltage conductor is electrically insulated from the first high voltage conductor. In an example, electrically insulating the first low voltage conductor from the first high voltage conductor effectively isolates the first low voltage conductor from the first high voltage conductor below an insulation breakdown voltage. In an example, the first low voltage electrode is spaced from the first high voltage electrode at a predetermined distance such that during delivery of a predetermined high voltage therapy, the maximum voltage difference between the first low voltage conductor and the first high voltage conductor does not exceed the insulation breakdown voltage. In an example, an insulative covering that extends over the high voltage conductor electrically isolates the first high voltage conductor from the low voltage conductor. In another example, both the low voltage conductor and the first high voltage conductor have an insulative covering.

At 750, a second low voltage conductor is coupled through the first lumen in the insulative tube to a second low voltage electrode proximate the first high voltage electrode. At 760, the second low voltage conductor is electrically insulated from the first high voltage conductor such that the second low voltage conductor is electrically isolated from the first high voltage conductor at potentials below the breakdown voltage of the insulation. In an example, the second low voltage conductor is electrically insulated from the first high voltage conductor at pacing or sensing voltages. FIG. 1 shows an example of a conductor that can be formed according to this method.

Alternatively, at 770, a second low voltage conductor is coupled through the second lumen in the insulative tube to a second low voltage electrode proximate the second high voltage conductor. At 780, the second low voltage conductor is electrically insulated from the second high voltage conductor, such that the second low voltage conductor is electrically isolated from the second high voltage conductor at potentials below a threshold. FIGS. 5A and 5B show examples of conductors that can be formed according to this method.

Figure 8:
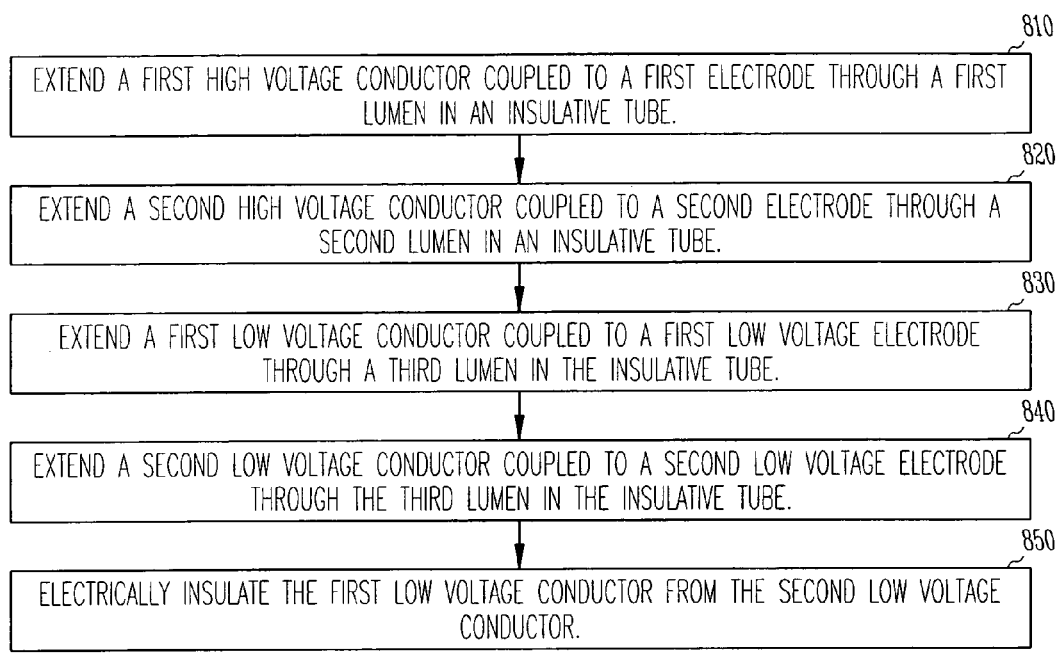
FIG. 8 is flow chart that illustrates a method of combining conductors in lumens in a lead assembly where high voltage conductors extend through first and second lumens and low voltage conductors are combined in a third lumen.

FIG. 8 is flow chart that illustrates another example method of combining conductors in lumens in a lead assembly. At 810, a first high voltage conductor coupled to a first electrode is extended through a first lumen in an insulative tube. At 820, a second high voltage conductor coupled to a second electrode is extended through a second lumen in an insulative tube such that the insulative tube provides an insulative layer between the first high voltage conductor and the second high voltage conductor. At 830, a first low voltage conductor coupled to a first low voltage electrode is extended through a third lumen in the insulative tube. At 840, a second low voltage conductor coupled to a second low voltage electrode is extended through the third lumen in the insulative tube. At 850, the first low voltage conductor is insulated from the second low voltage conductor. FIGS. 6A and 6B show examples of conductors that can be formed according to the method shown in FIG. 8.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim.

What is claimed is:

1. A medical device lead assembly comprising:
   a first high voltage electrode, a second high voltage electrode, and a first low voltage electrode, the first low voltage electrode proximate the first high voltage electrode;
   a tube having a first lumen and a second lumen;
   a first high voltage conductor extending through the first lumen and coupled to the first high voltage electrode;
   a second high voltage conductor extending through the second lumen and coupled to the second high voltage electrode; and
   a first low voltage conductor extending through the first lumen and electrically insulated from the first high voltage conductor, the first low voltage conductor coupled to the first low voltage electrode.

2. The medical device lead assembly of claim 1, wherein the first low voltage electrode is within about 1 inch of the first high voltage electrode.

3. The medical device lead assembly of claim 1, wherein the first low voltage conductor is electrically isolated from the first high voltage conductor up to an insulation breakdown voltage; and
   the first low voltage electrode is positioned with respect to the first high voltage electrode such that a maximum voltage difference between the first low voltage conductor and the first high voltage conductor does not exceed the insulation breakdown voltage during delivery of a high voltage therapy.

4. The medical device lead assembly of claim 1, further comprising a second low voltage electrode proximate the first high voltage electrode, and a second low voltage conductor extending through the first lumen and coupled to the second low voltage electrode.

5. The medical device lead assembly of claim 1, further comprising a second low voltage electrode proximate the second high voltage electrode, and a second low voltage conductor extending through the second lumen and electrically insulated from the second high voltage conductor.

6. The medical device lead assembly of claim 1, wherein the first low voltage conductor includes a conductive coil and an insulative sheath extending over the conductive coil.

7. The medical device lead assembly of claim 6, wherein the insulative sheath has a cylindrical outer surface and the first lumen has a first interior surface that defines a first partial cylinder having a diameter that is approximately the same as the diameter of the cylindrical outer surface of the insulative sheath.

8. The medical device lead assembly of claim 7, wherein the conductive coil is rotatable in the sheath with respect to an axis that is substantially parallel to an axis of the tube and the first interior surface of the first lumen resists rotational movement of insulative sheath relative to the tube when the coil is rotated.

9. The medical device lead assembly of claim 8, wherein the first high voltage conductor has an insulative coating having a cylindrical outer surface that contacts the sheath on the conductive coil, and the first lumen has a second interior surface that defines a second partial cylinder having a diameter that is approximately the same as the diameter of the cylindrical outer surface of the first high voltage conductor, wherein the second interior surface resists radial and rotational movement of the first high voltage conductor relative to the tube when the coil is rotated in the sheath.

10. The medical device lead assembly of claim 1, wherein the first high voltage electrode is a first defibrillation electrode, and the second high voltage electrode is a second defibrillation electrode.

11. The medical device lead assembly of claim 1, further comprising a medical device including an energy source, the lead assembly operatively coupled to the energy source.

12. The medical device lead assembly of claim 11, wherein the medical device is a defibrillator.

13. The medical device lead assembly of claim 1, wherein the first high voltage conductor has an insulative coating and the first low voltage conductor does not have an insulative coating, and wherein an outer surface of the insulative coating surrounding the first high voltage conductor is positioned adjacent an outer surface of the first low voltage conductor.

14. The medical device lead assembly of claim 1, wherein the first high voltage conductor and the first low voltage conductor each have an insulative coating, and wherein an outer surface of the insulative coating surrounding the first high voltage conductor is positioned adjacent an outer surface of the insulative coating surrounding the first low voltage conductor.

15. The medical device lead assembly of claim 1, wherein the first low voltage electrode is configured for at least one of sensing or pacing.

16. The medical device lead assembly of claim 1, wherein the second lumen is positioned proximate a bulge in the first lumen.

17. The medical device lead assembly of claim 1, wherein the first low voltage conductor is electrically insulated from the first high voltage conductor from the low conductor proximal end to the low conductor distal end.

18. A method comprising:
   extending a first high voltage conductor through a first lumen in an insulative tube for a medical device lead assembly;
   coupling the first high voltage conductor to a first high voltage electrode;
   extending a second high voltage conductor through a second lumen in the insulative tube;
   coupling the second high voltage conductor to a second high voltage electrode;
   extending through the first lumen in the insulative tube a first low voltage conductor;
   coupling the first low voltage conductor to a first low voltage electrode proximate the first high voltage electrode; and
   electrically insulating the first low voltage conductor from the first high voltage conductor, wherein the first low voltage conductor is electrically isolated from the first high voltage conductor.

19. The method of claim 18, wherein the electrically insulating the first low voltage conductor from the first high voltage conductor effectively isolates the first low voltage conductor from the first high voltage conductor below an insulation breakdown voltage; and
   further comprising spacing the first low voltage electrode from the first high voltage electrode at a predetermined distance such that during delivery of a predetermined high voltage therapy a maximum voltage difference between the first low voltage conductor and the first high voltage conductor does not exceed the insulation breakdown voltage.

20. The method of claim 19, wherein spacing the first low voltage electrode from the first high voltage electrode at a predetermined distance includes spacing the first low voltage electrode within about 1 inch of the first high voltage electrode on the insulative tube.

21. The method of claim 18, further comprising extending through the first lumen in the insulative tube a second low voltage conductor;
   coupling the second low voltage conductor to a second low voltage electrode; and
   electrically insulating the second low voltage conductor from the first high voltage conductor and the first low voltage conductor, wherein the second low voltage conductor is electrically isolated from the first high voltage and the first low voltage conductor.

22. The method of claim 18, further comprising extending a second low voltage conductor through the second lumen in the insulative tube;
   coupling the second low voltage conductor to a second low voltage electrode; and
   electrically insulating the second low voltage conductor from the second high voltage conductor, wherein the second low voltage conductor is electrically isolated from the second high voltage conductor.

23. The method of claim 18, wherein the first high voltage conductor is coupled to the first high voltage electrode after the first high voltage conductor is extended through the first lumen.

24. The method of claim 18, wherein electrically insulating the first low voltage conductor from the first high voltage conductor includes coating one or both of the first low voltage conductor or the first high voltage conductor with an insulative material.

25. The method of claim 24, wherein coating one or both of the first low voltage conductor or the first high voltage conductor with an insulative material includes coating one or both of the first low voltage conductor or the first high voltage conductor using at least one of ethylene-tetrafluoroethylene (ETFE) or polytetrafluoroethylene (PTFE).

26. The method of claim 24, wherein electrically insulating the first low voltage conductor form the first high voltage conductor includes positioning an outer surface of the insulative coating surrounding the first low voltage conductor adjacent an outer surface of the insulative coating surrounding the first high voltage conductor.

27. The method of claim 18, wherein electrically insulating the first low voltage conductor from the first high voltage conductor includes selecting an insulative material having an insulation breakdown voltage that exceeds a voltage difference between the first low voltage conductor and the first high voltage conductor during delivery of a predetermined high voltage therapy.

* * * * *